(12) United States Patent  
Yao et al.

(10) Patent No.: US 11,498,068 B2  
(45) Date of Patent: Nov. 15, 2022

(54) MICROFLUIDIC DEVICE AND DETECTION METHOD THEREFOR AND MICROFLUIDIC DETECTION ASSEMBLY

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Wenliang Yao, Beijing (CN); Haochen Cui, Beijing (CN); Peizhi Cai, Beijing (CN); Yuelei Xiao, Beijing (CN); Fengchun Pang, Beijing (CN); Yue Geng, Beijing (CN); Le Gu, Beijing (CN); Nan Zhao, Beijing (CN); Hui Liao, Beijing (CN); Yingying Zhao, Beijing (CN); Chuncheng Che, Beijing (CN)

(73) Assignees: BEIJING BOE OPTOELECTRONICS TECHNOLOGY CO., LTD., Beijing (CN); Beijing BOE Technology Development Co., Ltd., Beijing (CN)

( * ) Notice: Subject to any disclaimer, the term of this patent is extended or adjusted under 35 U.S.C. 154(b) by 478 days.

(21) Appl. No.: 16/632,931

(22) PCT Filed: Jan. 2, 2019

(86) PCT No.: PCT/CN2019/070123  
§ 371 (c)(1),  
(2) Date: Jan. 22, 2020

(87) PCT Pub. No.: WO2020/140204  
PCT Pub. Date: Jul. 9, 2020

(65) Prior Publication Data  
US 2021/0060555 A1    Mar. 4, 2021

(51) Int. Cl.  
*B01L 3/00* (2006.01)

(52) U.S. Cl.  
CPC . *B01L 3/502715* (2013.01); *B01L 2300/0645* (2013.01); *B01L 2300/088* (2013.01)

(58) Field of Classification Search  
CPC ....... B01L 3/502715; B01L 2300/0645; B01L 2300/088; B01L 2200/0668;  
(Continued)

(56) References Cited

PUBLICATIONS

Song et al. "Electromagnetic microfluidic cell labeling device using on-chip microelectromagnet and multi-layered channels" Sensors and Actuators B: Chemical vol. 141, Issue 1, Aug. 18, 2009, pp. 210-216 (Year: 2009).*

* cited by examiner

*Primary Examiner* — Benjamin R Whatley  
*Assistant Examiner* — Quocan B Vo  
(74) *Attorney, Agent, or Firm* — Collard & Roe, P.C.

(57) ABSTRACT

A microfluidic device, a microfluidic detection assembly and a detection method for the microfluidic device. The microfluidic device includes a first substrate and a second substrate; the first substrate and the second substrate are oppositely arranged to define a channel between the first substrate and the second substrate, the channel is configured for liquid to flow, the first substrate includes a base substrate and a plurality of control assemblies which are arranged on the base substrate along an extending direction of the channel, each of the plurality of control assemblies includes: a first electrode, a second electrode and a plurality of coils, and the first electrode is configured to input currents into the plurality of coils, and the plurality of coils are connected in parallel to the second electrode.

20 Claims, 5 Drawing Sheets

(58) Field of Classification Search
CPC ..... B01L 2300/0816; B01L 2300/0887; B01L 2400/043; B01L 3/502761; B03C 2201/18; B03C 2201/26; B03C 1/01; B03C 1/0335; B03C 1/288; G01N 33/54326; G01N 27/00
See application file for complete search history.

MICROFLUIDIC DEVICE AND DETECTION METHOD THEREFOR AND MICROFLUIDIC DETECTION ASSEMBLY

CROSS REFERENCE TO RELATED APPLICATIONS

This application is the National Stage of PCT/CN2019/070123 filed on Jan. 2, 2019, the disclosure of which is incorporated by reference.

TECHNICAL FIELD

The embodiments of the present disclosure relate to a microfluidic device and a detection method therefor and a microfluidic detection assembly.

BACKGROUND

Microfluidics is a technology that precisely controls and manipulates micro-scale fluids, and may integrate basic operation units used for, for example, sample preparation, reaction, separation, and detection in the biochemical analysis process on a micron-scale chip to automatically complete the entire analysis process. Microfluidics has the advantages of less sample consumption, a fast detection speed, being easy and simple to handle, integration of multiple functions, compactness, and portability, etc., and has great potential for application in the fields of biology, chemistry, medicine and so on.

SUMMARY

At least one embodiment of the present disclosure provides a microfluidic device, which includes a first substrate and a second substrate, wherein the first substrate and the second substrate are oppositely arranged to define a channel between the first substrate and the second substrate, and the channel is configured for liquid to flow, the first substrate comprises a plurality of control assemblies which are arranged along an extending direction of the channel, each of the plurality of control assemblies comprises: a first electrode, a second electrode and a plurality of coils, and the first electrode is configured to input currents into the plurality of coils, and the plurality of coils are connected in parallel to the second electrode.

In the microfluidic device according to some embodiments of the present disclosure, the plurality of coils are arranged in a same layer in the first substrate, and the plurality of coils are arranged in a row in a direction perpendicular to the extending direction of the channel.

In the microfluidic device according to some embodiments of the present disclosure, the plurality of coils and the second electrode are arranged in different layers of the first substrate, and the second electrode is electrically connected to the plurality of coils through via holes.

In the microfluidic device according to some embodiments of the present disclosure, the first electrode and the plurality of coils are arranged in a same layer of the first substrate.

In the microfluidic device according to some embodiments of the present disclosure, the first electrode and the plurality of coils are arranged in different layers of the first substrate, and the first electrode is electrically connected to the plurality of coils through via holes.

In the microfluidic device according to some embodiments of the present disclosure, a resistivity of a material of at least one of the first electrode and the second electrode is smaller than a resistivity of a material of the plurality of coils.

In the microfluidic device according to some embodiments of the present disclosure, the plurality of control assemblies share a same electrode as the first electrode of each of the plurality of control assemblies.

In the microfluidic device according to some embodiments of the present disclosure, the plurality of control assemblies share a same planar electrode as the second electrode of each of the plurality of control assemblies.

In the microfluidic device according to some embodiments of the present disclosure, a plurality of the control assemblies used for a plurality of the channels share a same planar electrode as the second electrode of each of the plurality of the control assemblies.

In the microfluidic device according to some embodiments of the present disclosure, the planar electrode is a slit electrode.

In the microfluidic device according to some embodiments of the present disclosure, the planar electrode overlaps with the plurality of coils of each of the plurality of control assemblies in a direction perpendicular to a surface of the first substrate.

The microfluidic device according to some embodiments of the present disclosure further includes a mixing assist structure, wherein the mixing assist structure is in the channel and configured to mixing the fluid.

In the microfluidic device according to some embodiments of the present disclosure, the mixing assist structure is on a surface of the second substrate facing the first substrate or on a surface of the substrate facing the second substrate.

In the microfluidic device according to some embodiments of the present disclosure, the mixing assist structure comprises a ∧-shaped protrusion, and the ∧-shaped protrusion points to a direction opposite to a direction in which the fluid is allowed to flow.

In the microfluidic device according to some embodiments of the present disclosure, each of the channel comprises an inlet and an outlet, the mixing assist structure comprises a ∧-shaped protrusion, and the ∧-shaped protrusion points to the inlet of the channel in which the ∧-shaped protrusion is located.

In the microfluidic device according to some embodiments of the present disclosure, the mixing assist structure is arranged before and/or after at least one of the plurality of control assemblies in a direction in which the fluid is allowed to flow.

The microfluidic device according to some embodiments of the present disclosure further includes: a spacer, wherein the spacer is at opposite sides of the channel and between the first substrate and the second substrate, and the spacer, the first substrate and the second substrate define the channel.

At least one embodiment of the present disclosure further provides a microfluidic detection assembly, which includes:

any of the above-mentioned microfluidic devices; and a magnetic particle, configured to move in the channel of the microfluidic device in an operation.

At least one embodiment of the present disclosure further provides a detection method for any of the above-mentioned microfluidic devices, the detection method including:

providing, in the channel, a solution comprising a detection sample and a magnetic particle, the magnetic particle being capable of being bound with the detection sample;

providing an electric current to the coil through the first electrode and the second electrode to cause the magnetic particle with the detection sample bound to a surface of the magnetic particle to be attracted in a magnetic field generated by the coil; and discharging the solution in the channel to obtain the magnetic particle with the detection sample bound to the surface of the magnetic particle.

BRIEF DESCRIPTION OF THE DRAWINGS

In order to clearly illustrate the technical solution of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

Figure 1:
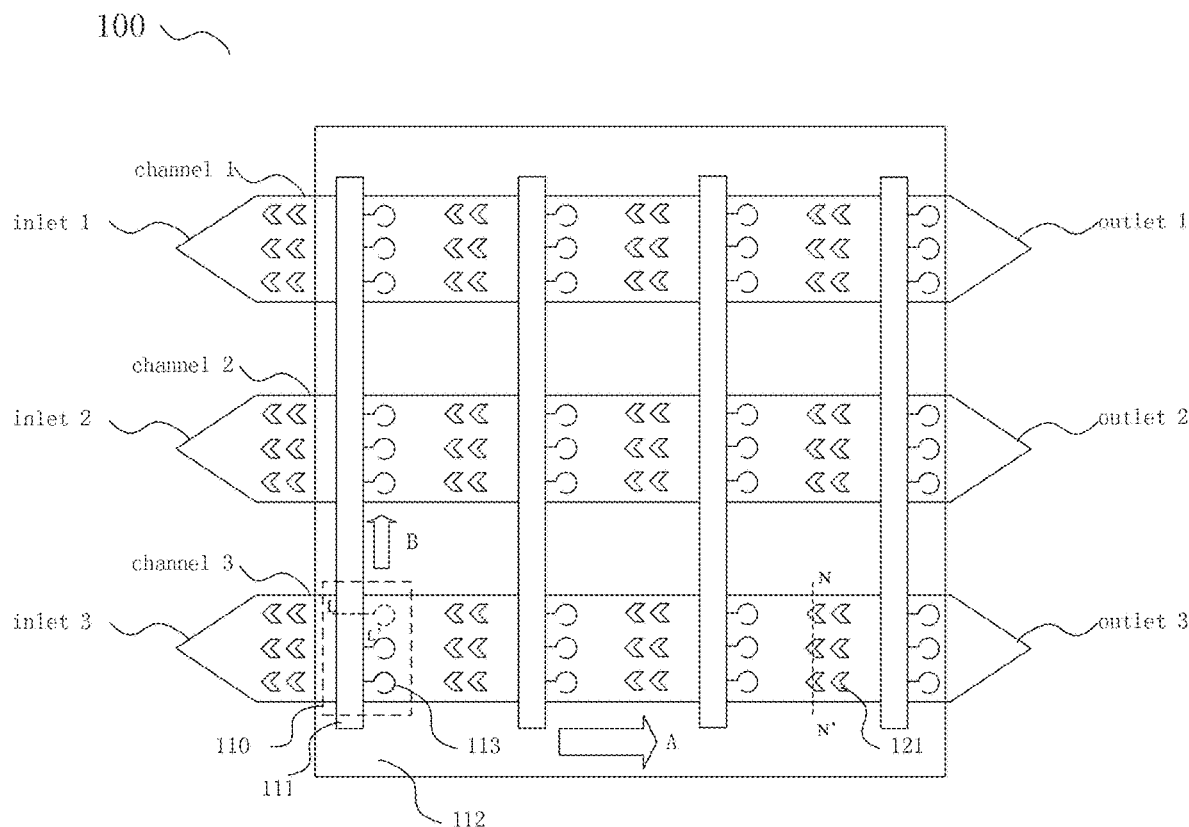
FIG. 1 is a schematic planar structural diagram of a microfluidic device according to some embodiments of the present disclosure.

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Microfluidics may adopt magnetic particles such as magnetic beads to carry samples. For example, magnetic beads are magnetic oxide grains, a surface of which may be covered by functional groups, thereby forming special structural particles with certain magnetism, such as having the characteristics of macromolecule microballoons. The functional groups mainly include amido, carboxyl, thio and so on, and the coupling reaction may occur among the functional groups and a small biological molecule such as a protein, a nucleic acid, a catalyzing enzyme, without affecting their activity. Superparamagnetic beads may be quickly separated from the dispersion medium under the action of a magnetic field, and when the external magnetic field is removed, the superparamagnetic beads have no remanent magnetism and are suspended in the solution again. The large surface area of magnetic beads increase the effective area for the biochemical reaction. In immunoassays, the antibody on the beads is specifically bound with the protein to be tested, and forms an antigen-antibody-magnetic bead compound, thereby realizing separation from other substances. The captured antigen may also continue to react with a secondary antibody or a chemiluminescent substrate in a reagent, thereby amplifying the detection signal and achieving a quantitative analysis.

The microfluidic immunoassay technology based on the magnetic beads capture involves introducing the controllable magnetic field in a chip to control the magnetic beads. The design of the magnetic field is mainly divided into two categories: the first is providing an external permanent magnet or electromagnet and a control system therefor at a particular position of the chip, and the second is integrating a planar electromagnetic coil in the chip and generating a magnetic field in the coil by applying a constant current. The external permanent magnet or electromagnet generates a stable magnetic field and a large magnetic induction intensity. However, the magnetic field intensity is fixed and short of adjustability, and the integrated level of the chip is not high, and the peripheral control system is complicated, which limits the application of the methods in the field of immunoassay and instant diagnosis (POCT). The planar electromagnetic coil technology uses photolithograph, sputtering, electroplating and other processes to combine metal wires with micro-channel processes, resulting in a high degree of integration. By applying different working currents to the particular coils, the flexible control of the position and the magnetic induction intensity of the magnetic field is achieved, and the complexity degree of the peripheral system is reduced, which represents the development direction of the instant diagnosis technology. However, the planar electromagnetic coil generates a large amount of heat during the energization process. DNA, the protein molecules and other samples participating in biochemical reactions are quite sensitive to the change of temperature. The large amount of heat may unexpectedly affect experimental results.

At least one embodiment of the present disclosure provides a microfluidic device including a first substrate and a second substrate. The first substrate and the second substrate are oppositely arranged to define a channel between the first substrate and the second substrate. The channel is used for liquid to flow. The first substrate includes a plurality of control assemblies which are arranged in the extending direction of the channel, and each control assembly includes a first electrode, a second electrode and a plurality of coils. The first electrode is used to input currents to the plurality of coils, and the plurality of coils are connected to the second electrode in parallel.

At least one embodiment of the present disclosure also provides a microfluidic detection assembly including the microfluidic device and a detection method used for the microfluidic device.

FIG. 1 is a schematic planar structural diagram of the microfluidic device according to some embodiments of the present disclosure. A microfluidic device 100 according to some embodiment of the present disclosure as shown in FIG. 1 includes a first substrate and a second substrate. The first substrate and the second substrate are oppositely arranged to define three channels which are distributed side by side between the first substrate and the second substrate, and each channel includes its own inlet and outlet. A solution including a detection sample and magnetic-particle such as magnetic beads is allowed to enter the channel from the inlet of the channel and flow to the outlet of the channel in the direction as shown by an arrow A.

The microfluidic device 100 may include a driving device (not show) used for driving the liquid to flow in the channel, and the driving device may include, for example, a pump, a vacuum generator and so on, which is not limited in the embodiments of the present disclosure.

Furthermore, the microfluidic device 100 may also include a light source, a detection device and the like for performing the biochemical detection. The light source may be, for example, a point light source, a line light source, a surface light source, and the like. The light source may be, for example, a light-emitting diode, a cold cathode fluorescent lamp, an electroluminescent illuminant, a flat fluorescent lamp, a laser light source, or the like, and the emitted light may be visible light, infrared light, or the like, which is not limited in the embodiments of the present disclosure. The detection device may include, for example, an optical sensor, a temperature sensor and so on. The optical sensor may be, for example, a photosensitive diode, a phototransistor and so on. For example, the photosensitive diode may be a PIN-type diode, a PN-type diode and so on, it may be a silicon-based diode, or a non-silicon-based diode and so on, and the embodiments of the present disclosure does not limited the specific type and structure of a light receiver.

It could be understood that the three channels as shown in FIG. 1 are only illustrative, and in other embodiments, the microfluidic device 100 may include more or less channels as required, therefore, cross contamination between samples may be avoided, and the detection efficiency may be improved, which is not limited in the embodiments of the present disclosure.

The first substrate includes a plurality of control assemblies 110 (as shown as dotted blocks in FIG. 1) arranged along an extending direction (as shown indicated by an arrow A in FIG. 1) of the channel, and each control assembly 110 includes a first electrode 111, a second electrode 112 and a plurality of coils 113. The first electrode 111 is used for inputting currents to the plurality of coils 113, and the plurality of coils 113 are connected to the second electrode 113 in parallel. The plurality of coils 113 is energized to generate the magnetic field which is used to capture the magnetic beads in the solution.

In some embodiments, the plurality of coils 113 in each control assembly 110 are arranged on the same layer in the first substrate (that is, the plurality of coils 113 are formed by a single patterning process using the same material) and the plurality of coils, for example, are arranged in a row in a direction (for example, a direction shown by an arrow B in FIG. 1) perpendicular to the extending direction (for example, a direction shown by an arrow A in FIG. 1) of the channel. For example, in the embodiments shown in FIG. 1, in each control assembly 110, three coils 113 are arranged in a row in the direction perpendicular to the extending direction of the channel. The working area of the magnetic field may be expanded by providing a plurality of coils in the direction perpendicular to the extending direction of the channel. Furthermore, flexible control of the capture array may be achieved by setting the number of channels of the microfluidic device, the number of control assemblies arranged along the extending direction of the channel, and the number of coils arranged in a row in each control assemblies in a direction perpendicular to the extending direction of the channel.

It could be understood that each control assembly 110 in the FIG. 1 including three coils is only illustrative, in other embodiments, the control assembly 110 may include more or less coils as required, and the embodiments of the present disclosure have no limitation in this aspect.

The plurality of coils 113 in each control assembly 110 may be arranged in the same layer as the first electrode 111 (that is, the plurality of coils 113 and the first electrode 111 are formed by using the same material through the same patterning process) or in the different layer. In a case where the plurality of coils 113 and the first electrode 111 are located in different layers, the first electrode may be electrically connected to the plurality of coils 113 through a via hole. Furthermore, the plurality of coils 113 and the second electrode 112 in each control assembly 110 may be located in the different layer in the first substrate, and the second electrode 112 may be electrically connected to each of the plurality of coils 113 through a via hole.

Figure 2:
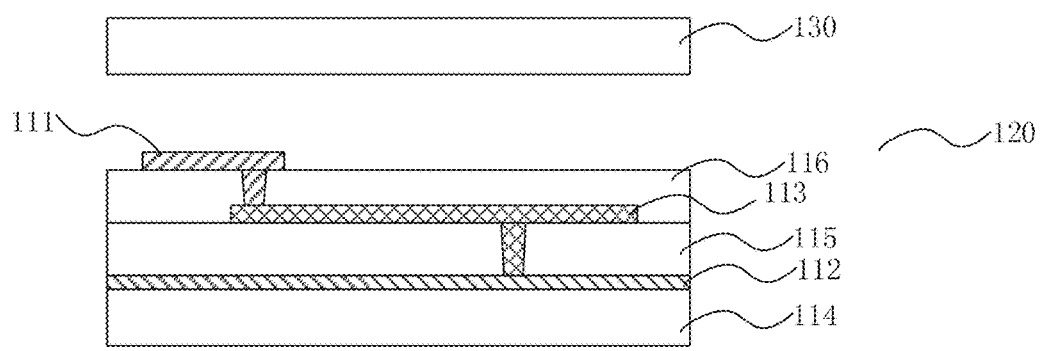
FIG. 2 is a schematic cross-sectional diagram taken along line L-L' in FIG. 1 according to some embodiments of the present disclosure.

FIG. 2 is a schematic cross-sectional diagram taken along line L-L' in FIG. 1 according to some embodiments of the present disclosure. As shown in FIG. 2, a first substrate 120 and a second substrate 130 are arranged opposite to each other to define a channel for liquid to flow between the first substrate 120 and the second substrate 130. The coil 113 and a second electrode 112 are electrically connected through the via hole formed in a first insulating layer 115, and the first electrode 111 and the coil 113 are electrically connected through the via hole formed in a second insulating layer 116. The first electrode 111, the second electrode 112 and the coil 113 are formed in the different layers respectively.

For example, in the embodiment shown in FIG. 2, the first substrate 120 may also include a base substrate 114, a first insulating layer 115, and a second insulating layer 116. The second electrode 112 is provided on the base substrate 114. In some embodiments, the second electrode 112, for example, is formed on the base substrate 114 by physical vapor deposition (PVD), printing (for example, inkjet printing), coating, sputtering, photolithography, and the like. The second electrode 112 may be formed as a planar electrode or a pattern electrode. The thickness of the second electrode 112 may be, for example, 1 micrometre. The first insulating layer 115 is provided on the second electrode 112. In some embodiments, the first insulating layer 115 may also be provided on the second electrode 112 by, for example, physical vapor deposition (PVD), printing (for example, inkjet printing), coating, sputtering, and the like, and for example, the via hole is formed in the first insulating layer 115 by an etching process. The coil 113 is provided on the first insulating layer 115. In some embodiments, the coils 113 is formed on the first insulating layer 115 by, for example, physical vapor deposition (PVD), printing (for example inkjet printing), coating, sputtering, photolithography, and the like. In some embodiments, the coils 113 is, for example, formed into a ring shape with an opening, such as the coil 113 is formed as a 3/4 ring, a 4/5 ring, or the like;

in other embodiments of the present disclosure, the coil 113 is formed as a multi-turn coil, which is not limited by the embodiments of the present disclosure. The coil 113 is electrically connected to the second electrode 112 through the via hole in the first insulating layer 115. The second insulating layer 116 is provided on the coil 113. In some embodiments, the second insulating layer 116 may also be provided on the coil 113 by, for example, physical vapor deposition (PVD), printing (for example inkjet printing), coating, sputtering, and the like, and for example, the via hole may be formed in the second insulating layer 116 by an etching process. The first electrode 111 is provided on the second insulating layer 116, and is electrically connected to the coil 113 through a via hole in the second insulating layer 116. In some embodiments, the first electrode 111 is provided on the second insulating layer 116 by, for example, physical vapor deposition (PVD), printing (for example, inkjet printing), coating, sputtering, photolithography, and the like. The thickness of the first electrode 111 may be, for example, 500 nanometers, and the width of the first electrode 111 in the extending direction of the channel may be, for example, 200 micrometres.

In some embodiments, for example, the second electrode 112, the first insulating layer 115, the coil 113, the second insulating layer 116, and the first electrode 111, which are prepared in advance, may be respectively transferred and adhered to the base substrate 114, the second electrode 112, the first insulating layer 115, the coil 113, and the second insulating layer 116 by an adhesive, which are not limited in the embodiments of the present disclosure.

The base substrate 114 may be made of, for example, glass, ceramics, silicon, polyimide and so on, and the base substrate 114 may be also covered with a buffer layer or the like as required, and then functional structures such as electrodes are formed on the buffer layer. The first electrode 111, the second electrode 112 and the coil 113 may be made of any suitable conducting material, for example, metal, metal alloy, indium oxide tin (ITO) and so on. The first insulating layer 115 and the second insulating layer 116 may be formed of, for example, an inorganic insulating material or an organic insulating material, for example, resin, silicon nitride and the like. The second substrate 130 is made of, for example, glass, ceramics, silicon, polyimide and so on. The second substrate 130 and the base substrate 114 may be formed of the same material or different materials, which is not limited in the embodiments of the present disclosure.

Furthermore, the substrate 120 may also include an insulating layer (not shown) covering the first electrode 111 to insulate the first electrode 111 from the liquid in the channel and prevent the first electrode 111 from being contaminated.

In the embodiment shown in FIG. 2, an end of the coil 113 and the first electrode 111 are electrically connected through the via hole in the second insulating layer 116, and the other end of the coil 113 is electrically connected to the second electrode 112 through the via hole in the first insulating layer 115. In some embodiments, the first electrode 111 may be used to input the control current, and the second electrode 112 may be used as a grounding electrode. In the case where the first electrode 111 inputs a control current to the coil 113, the current in the coil 113 may generate a magnetic field, which may apply a magnetic force to the magnetic beads in the liquid in the channel, and in a case where the magnetic force exerted by the magnetic field on the magnetic beads is greater than the fluid viscous force that the magnetic beads are subject to in the liquid, the magnetic beads may be trapped in the magnetic field generated by the current in the coil 113.

Figure 3:
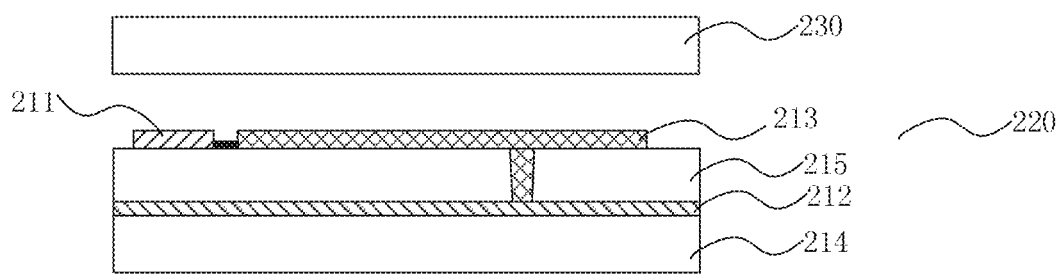
FIG. 3 is a schematic cross-sectional diagram taken along line L-L' in FIG. 1 according to some other embodiments of the present disclosure.

FIG. 3 is a schematic cross-sectional diagram taken along line L-L' in FIG. 1 according to some other embodiments of the present disclosure. The embodiment shown in FIG. 3 is substantially the same as the embodiment shown in FIG. 2, except that the first electrode 211 and the coil 213 are both formed on the first insulating layer 215 in FIG. 3, and the first substrate 220 does not include the second insulating layer 116 in the embodiment shown in FIG. 3. For example, the first electrode 211 and the coil 213 may be arranged in the same layer, that is, the first electrode 211 and the coil 213 may be formed by using the same material through a single patterning process. The first electrode 211 and the coil 213 may electrically connected by a wire. The first electrode 111 and the coil 213 may be made of any suitable conducting material, for example, metal, metal alloy, indium oxide tin (ITO) and so on. In some embodiments, the first electrode 211 and the coil 213 are provided respectively on the first insulating layer 215 by, for example, physical vapor deposition (PVD), printing (for example inkjet printing), coating, sputtering, photolithography, and the like. The detailed descriptions of the first electrode 211, the second electrode 212, the coil 213, the base substrate 214, the first insulating layer 215, and the second substrate 230 in FIG. 3 may refer to the above descriptions of the first electrode 111, the second electrode 112, the coil 113, the base substrate 114, the first insulating layer 115, and the second substrate 130, which will not be repeated in the present disclosure.

Figure 4:
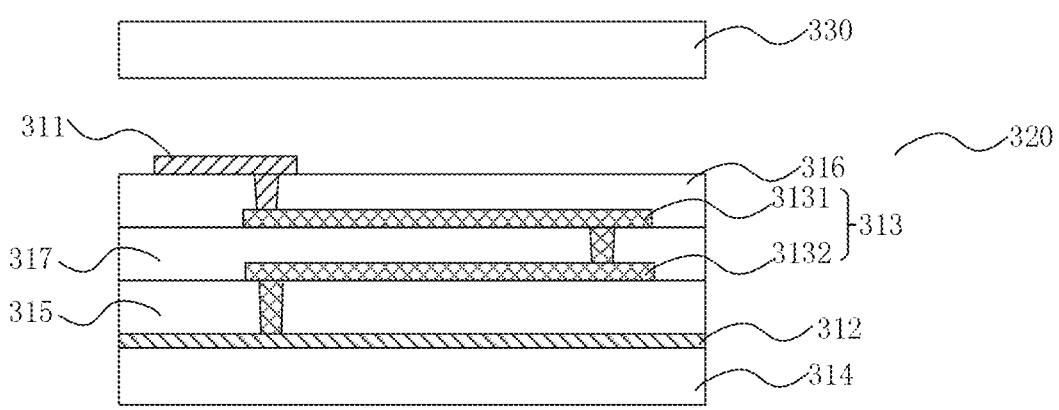
FIG. 4 is a schematic cross-sectional diagram taken along line L-L' in FIG. 1 according to some other embodiments of the present disclosure.

FIG. 4 is a schematic cross-sectional diagram taken along line L-L' in FIG. 1 according to some other embodiments of the present disclosure. The embodiment shown in FIG. 4 is substantially the same as the embodiment shown in FIG. 2, except that the coil 313 is a multi-layer coil and forms a three-dimensional spiral shape as shown in FIG. 4. For example, the coil 313 includes a first portion 3131 and a second portion 3132, and the first portion 3131 and the second portion 3132 are arranged in different layers and are electrically connected through a via hole, and the microfluidic device also includes a third insulating layer 317 between the first portion 3131 and the second portion 3132. The first portion 3131 and the second portion 3132 may be made of any suitable conducting material, for example, metal, metal alloy, indium oxide tin (ITO) and so on. The first portion 3131 and the second portion 3132 may be formed of the same material or different conducting materials, which is not limited in the embodiments of the present disclosure. The first portion 3131 and the second portion 3132 are provided respectively on the third insulating layer 317 and the first insulating layer 315 by, for example, physical vapor deposition (PVD), printing (for example inkjet printing), coating, sputtering, photolithography, and the like. The first portion 3131 and the second portion 3132 are electrically connected through a via hole formed in the third insulating layer 317. The third insulating layer 317, the first insulating layer 315 and/or the second 316 may be formed of the same material or different materials, which is not limited in the embodiments of the present disclosure. The detailed descriptions of the first electrode 311, the second electrode 312, the base substrate 314, the first insulating layer 315, the second insulating layer 316, and the second substrate 330 shown in FIG. 4 may refer to the above descriptions of the first electrode 111, the second electrode 112, the coil 113, the base substrate 114, the first insulating layer 115, the second insulating layer 116 and the second substrate 130, which will not be repeated in the present disclosure.

Figure 5:
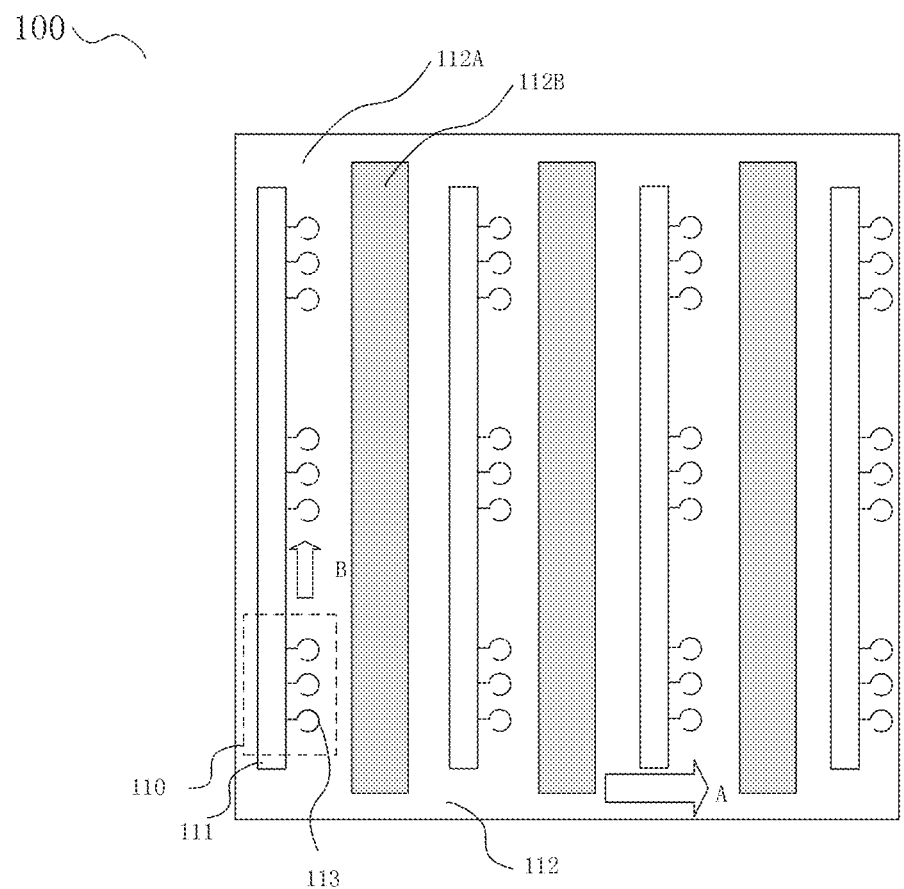
FIG. 5 is a schematic planar structural diagram of a microfluidic device according to some other embodiments of the present disclosure.

In some embodiments, as shown in FIG. 1, the second electrode 112 may be formed as a planar electrode on the base substrate 114. Each coil 113 in the control assembly 110 is connected through a via hole to the second electrode 112 formed as a planar electrode, that is, the plurality of coils 113 in the control assembly 110 are connected in parallel to the same second electrode 112 formed as a planar electrode, and the second electrode 112 formed as a planar electrode is shared by the plurality of coils 113. In the case where the microfluidic device 100 includes a plurality of control assemblies 110, the plurality of coils 113 of each of the plurality of control assembly 110 may be connected in parallel to the same second electrode 112 formed as the planar electrode, that is, the same planar electrode is used as the second electrode of each of the plurality of control assembly 110. For example, the microfluidic device 100 may include a plurality of channels, and the plurality of control assemblies 100 for the plurality of channels may share the same planar electrode as a second electrode of each of the plurality of control assemblies 100. As shown in FIG. 5, in some embodiments, the above-mentioned planar electrode may be a slit electrode so that the material forming the planar electrode may be reduced. For clarity, FIG. 5 is a simplified planar structural diagram of a microfluidic device according to some embodiments of the present disclosure, in which some elements are omitted. As shown in FIG. 5, the second electrode 112 formed as a slit electrode may include a non-slit portion 112A and a slit portion 112B.

As shown in FIG. 1, the projection of the plurality of coils 113 of each control assembly 110 on the base substrate 114 may at least partially overlap the projection of the second electrode 112 formed as a planar electrode on the base substrate 114. As shown in FIG. 5, in the case where the second electrode 112 is a slit electrode, the projection of the plurality of coils 113 of each control assembly 110 on the base substrate 114 may at least partially overlap the projection of non-slit portion 112B of the slit electrode on the base substrate 114.

The plurality of coils are connected to the same second electrode in parallel, and the coils share the second electrode, so the system resistance of the microfluidic device may be reduced, the thermal effect of the microfluidic device may be reduced, and the detection quality may be improved.

In the embodiment shown in FIG. 1 and FIG. 5, the microfluidic device 100 may include a plurality of channels, and each channel includes a plurality of control assemblies 110, so that the plurality of control assemblies 110 in the microfluidic device 100 may be arranged in an array, and, for example, the first electrodes 111 of a plurality of control assemblies 110 arranged in a row in a direction (such as a direction shown by an arrow B in FIG. 1 and FIG. 5) perpendicular to an extending direction of the channel (such as a direction shown by arrow A in FIG. 1 and FIG. 5) may be formed as a single electrode, that is, the same electrode is used as the first electrode of each of the plurality of control assemblies 110 provided in a row in a direction perpendicular to the extending direction of the channel, which may realize the synchronization control of multiple channels.

Although in the embodiments shown in FIG. 1 and FIG. 5, the plurality of coils 113 in each control assembly 110 are connected to the same first electrode 111, in some other embodiments, the plurality of coils 113 in each control assembly 110 may be connected to different first electrodes 111 as required. That is, the plurality of coils 113 in each control assembly 110 may receive different control currents to achieve more precise control, which is not limited in the embodiments of the present disclosure.

The size of the coil 113 is usually on the order of micrometres (for example, the diameter of the coil 113 is 80 micrometres, the line width of the coil is 20 micrometres, a capture area with a diameter of about 40-50 micrometres is formed), the heat productivity is small, and the electrode connected to the coil 113 (that is, the first electrode 111 and the second electrode 112) is the main source of heat, so in some embodiments, the resistivity of the material of at least one of the first electrode 111 and the second electrode 112 is smaller than that of the material of the coil 113, so that the first electrode 111 and the second electrode 112 generate less Joule heat during operations. For example, the first electrode 111 and the second electrode 112 may be made of copper, and the coil 113 may be made of aluminum. The material of the first electrode 111 and the second electrode 112 may be the same or different, which is not limited in the embodiments of the present disclosure.

The microfluidic device 100 provided by some embodiments of the present disclosure may also include a mixing assist structure which is configured to facilitate mixing of liquids in the channel and also located in the channel. The mixing assist structure may be located at a surface of the second substrate 130 facing the first substrate 120, or the mixing assist structure may be located at a surface of the first substrate 120 facing the second substrate 130, or the mixing assist structure may be located at the surface of the second substrate 130 facing the first substrate 120 and the surface of the first substrate 120 facing the second substrate 130.

The mixing assist structure may be an active mixing structure or a passive mixing structure. The active mixing structure may include: a mixing structure that uses ultrasonic waves to drive liquid to move, a mixing structure that uses electroosmosis to drive liquid to move, and the like. The passive mixing structure may include: a mixing structure in which liquids are mixed by dividing the liquid into layers, a mixing structure in which liquids are mixed by forming chaotic convection in the liquid, and the like.

As shown in FIG. 1, in some embodiments, the above-mentioned mixing assist structure includes ∧-shaped protrusions 121. In the other embodiments, the mixing assist structure may also include, for example, Z-shaped protrusions or S-shaped protrusions, which are not limited in the embodiments of the present disclosure. The ∧-shaped protrusion 121 is directed in a direction opposite to the direction that allows liquid to flow (that is, the direction from the channel inlet to the channel outlet, such as the direction indicated by an arrow A in FIG. 1), that is, the opening direction of the ∧-shaped protrusion 121 is directed to a direction that allows liquid to flow (for example, a direction indicated by an arrow A in FIG. 1). In some embodiments, the ∧-shaped protrusion 121 may point to the inlet of the channel. The ∧-shaped protrusion 121 may be located at a surface of the second substrate 130 facing the first substrate 120, or the ∧-shaped protrusion 121 may be located at a surface of the first substrate 120 facing the second substrate 130, or the ∧-shaped protrusion 121 may be located at the surface of the second substrate 130 facing the first substrate 120 and the surface of the first substrate 120 facing the second substrate 130.

In a case where the ∧-shaped protrusion 121 is located at the surface of the second substrate 130 facing the first substrate 120, the ∧-shaped protrusion 121 protrudes from the surface of the second substrate 130 facing the first substrate 120 toward the first substrate 120. In a case where the ∧-shaped protrusion 121 is located at the surface of the second substrate 130 facing the second substrate 130, the ∧-shaped protrusion 121 protrudes from the surface of the second substrate 130 facing the second substrate 130 toward the second substrate 130. The ∧-shaped protrusion 121 may be arranged at the first substrate 120 and/or the second substrate 130 by, for example, printing, coating, photolithograph and so on.

Figure 6:
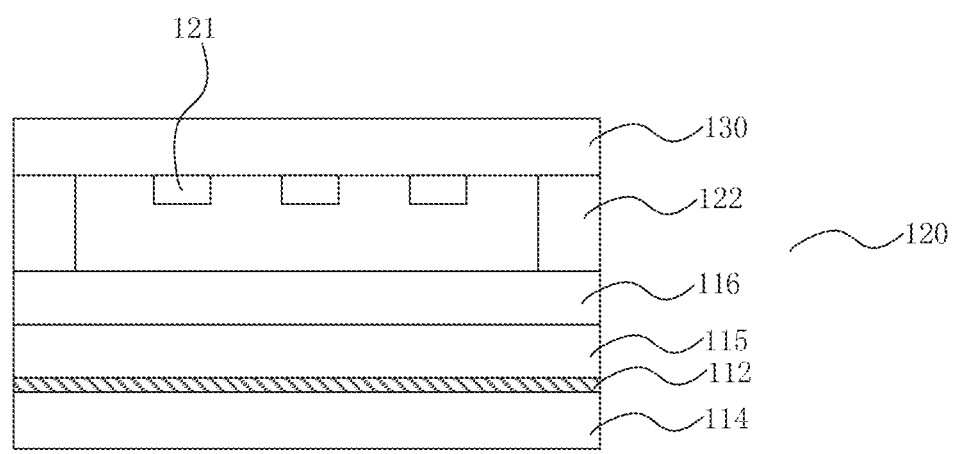
FIG. 6 is a schematic cross-sectional diagram taken along line N-N' in FIG. 1 according to some embodiments of the present disclosure.

FIG. 6 is a schematic cross-sectional diagram taken along line N-N' in FIG. 1 according to some embodiments of the present disclosure. As shown in FIG. 6, in a case where the ∧-shaped protrusion 121 is located at the surface of the second substrate 130 facing the first substrate 120, the ∧-shaped protrusion 121 protrudes from the surface of the second substrate 130 facing the first substrate 120 toward the first substrate 120. In addition, FIG. 6 also shows spacers 122 arranged on both sides of the channel between the first substrate 120 and the second substrate 130, which will be described in detail below.

As an example, the ∧-shaped protrusion 121 may have a length of 2 mm (the length refers to the length of the projection of the ∧-shaped protrusion 121 in the extending direction of the channel (such as the direction indicated by an arrow A in FIG. 1)), and a width of 1 mm (the width refers to a length of the projection of the ∧-shaped protrusion 121 in a direction (such as the direction indicated by an arrow B in FIG. 1) perpendicular to the extending direction of the channel (such as the direction indicated by an arrow A in FIG. 1) in the plane where the first substrate 120 is located), and a height of 30 um (the height refers to the distance between the surface of the ∧-shaped protrusion 121 facing the base substrate 114 and the surface of the ∧-shaped protrusion 121 away from the base substrate 114).

In some embodiments, in a direction that allows liquid to flow, a mixing assist structure is arranged before and/or after at least one of the plurality of control assemblies 110 in the microfluidic device 100. As in the embodiment shown in FIG. 1, in a direction that allows liquid to flow (for example, a direction indicated by an arrow A in FIG. 1), the ∧-shaped protrusions 121 are arranged before and after each control assembly 110.

In addition, in some embodiments, the microfluidic device 100 may also include a spacer between the first substrate 120 and the second substrate 130 to define a gap between the first substrate 120 and the second substrate 130. For example, the spacer may have a height of 50 micrometres, or the height of the spacer may be 40 micrometres, 30 micrometres, or the like. The spacer may be formed at the first substrate 120 and/or the second substrate 130 by, for example, printing, coating, photolithograph and so on. The spacer may be formed of, for example, resin. The spacer may be arranged at an edge of the first substrate 120 and/or the second substrate 130, or the spacer may be arranged at opposite sides of the channel to define the channel together with the first substrate 120 and the second substrate 130, and the embodiments of the present disclosure have no limitation in this aspect. The spacer 122 shown in FIG. 6 is an example of the above-mentioned spacer, and the spacer 122 is arranged at opposite sides of the channel between the first substrate 120 and the second substrate 130 to define the channel together with the first substrate 120 and the second substrate 130.

Figure 7:
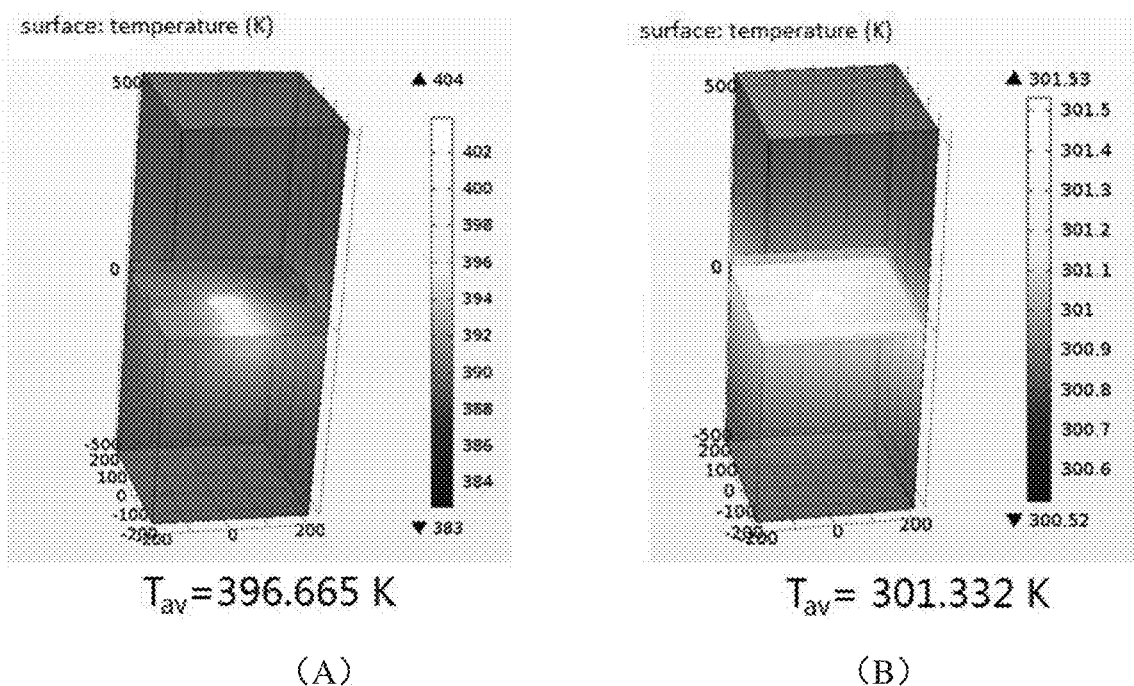
FIG. 7 shows a temperature distribution of the working area of a microfluidic device according to some embodiments of the present disclosure and a temperature distribution of working area of a microfluidic device in the related art.

FIG. 7 illustrates a temperature distribution of the working area of a microfluidic device according to some embodiments of the present disclosure and a temperature distribution of a working area of a microfluidic device in the related art. The working area of the above-mentioned microfluidic device refer to a column area with the center of the planar area surround by a coil of the microfluidic device (e.g., the center) as the center of the bottom, a semidiameter of 20 micrometres, and a height of 5.5 micrometres. Part (A) in FIG. 7 corresponds to a microfluidic device having a structure in which a coil and two electrodes connected to the ends of the coil are disposed in the same layer, the coil in the microfluidic device corresponding to part (A) in FIG. 7 is a copper ring with a diameter of 80 micrometres, a line width of 20 micrometres, a thickness of 500 nanometers, and a shape of a 4/5 ring, and the two electrodes connected to the ends of the coil are aluminium electrodes with a length of 2 mm, a thickness of 500 nanometers, and a width of 200 micrometres. Part (B) in FIG. 7 corresponds to a microfluidic device as shown in FIG. 2, the coil 113 in the microfluidic device corresponding to Part (B) in FIG. 7 is a copper ring with a diameter of 80 micrometres, a line width of 20 micrometres, a thickness of 500 nanometers, and a shape of a 4/5 ring, the first electrode 111 is an aluminium electrode with a width of 200 micrometres in an extending direction of the channel and a thickness of 500 nanometers in a direction perpendicular to a surface of the base substrate 114, and the second electrode is an aluminum electrode with a thickness of 1 micrometer in a direction perpendicular to a surface of the base substrate 114. Part (A) of FIG. 7 shows the temperature distribution of the working area of the microfluidic device in the related art in a case where the current input to the coil is 0.2 A, and Part (B) of FIG. 7 shows the temperature distribution of the working area of the microfluidic device according to some embodiments of the present disclosure in a case where the current input to the coil is 0.2 A. As shown in Part (A) of FIG. 7, in a steady state, the microfluidic device in the related art has an average temperature of 396.665K in the working area in a case where the current input into the coil is 0.2 A, and the temperature is much higher than the maximum temperature at which inactivation of various protease occurs, thereby making the microfluidic device in the related at unsuitable for immunoassays such as chemiluminescence. As shown in part (B) of FIG. 7, in a steady state, the microfluidic device according to some embodiments of the present disclosure has an average temperature of 301.332K in the working area in a case where the current input into the coil is 0.2 A, and the temperature meets the temperature requirements of various immunoassays. It can be seen that, in the microfluidic device according to the embodiments of the present disclosure, the amount of heat generated is greatly reduced, and the temperature of the working area of the microfluidic device is reduced, so that the microfluidic device can be applied to various types of immunoassays.

Figure 8:
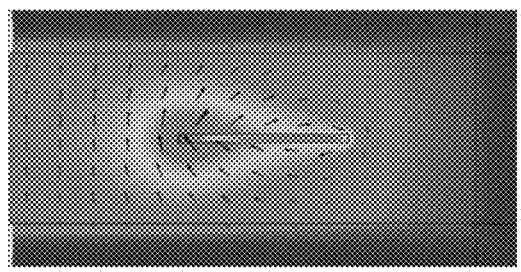
FIG. 8 is a magnetic flux density distribution diagram of a coil in the microfluidic device according to some embodiments of the present disclosure.

FIG. 8 is a magnetic flux density distribution diagram of a coil in the microfluidic device according to some embodiments of the present disclosure. The microfluidic device according to some embodiments of the present disclosure corresponding to FIG. 8 has the same structure as the microfluidic device according to some embodiments of the present disclosure corresponding to part (B) of FIG. 7 described above, and the repeated description is omitted herein. FIG. 8 shows the values and directions of the magnetic flux densities at different positions around a coil (in this example, the coil is a copper ring with a diameter of 80 micrometres, a line width of 20 micrometres, a thickness of 500 nanometers and a shape of a 4/5 ring) of a microfluidic device according to some embodiments of the present disclosure in a case where the current input into the coil is 0.2 A. Table 1 below shows the values of the magnetic flux densities at different positions from the center of the coil.

TABLE 1

| Distance from the center (micrometer) | magnetic flux density (Tesla) |
| --- | --- |
| 2 | 0.0041168 |
| 3 | 0.0041366 |
| 4 | 0.0041572 |
| 5 | 0.0041878 |
| 6 | 0.0042257 |
| 7 | 0.0042717 |
| 8 | 0.0043261 |
| 9 | 0.0043892 |
| 10 | 0.0044618 |
| 11 | 0.0045444 |
| 12 | 0.0046374 |

As shown in FIG. 8 and Table 1, in the microfluidic device according to some embodiments of the present disclosure, the magnetic field around the coil is substantially uniformly distributed, that is, the structure of the microfluidic device according to some embodiments of the present disclosure does not affect the distribution of the magnetic field.

In the microfluidic device provided by the embodiments of the present disclosure, the second electrode is shared by connecting the coils in parallel with the second electrode to reduce the heat productivity of the microfluidic device and to ensure the activity of the biological sample, and the control components are arranged in an array to increase the working area of the magnetic field and achieve flexible control of the capture area.

In some embodiments of the present disclosure, there is also provided a microfluidic detection assembly, including: any one of the above-mentioned microfluidic devices; and magnetic particles configured to move in a channel of the microfluidic device in an operation. The microfluidic device may be combined with the magnetic-particles to obtain, for example, a test suite which is provide to users. The magnetic particles may be, for example, magnetic beads, and the magnetic beads may be suitable for any kinds of beads, which are not limited in the embodiments of the present disclosure.

Figure 9:
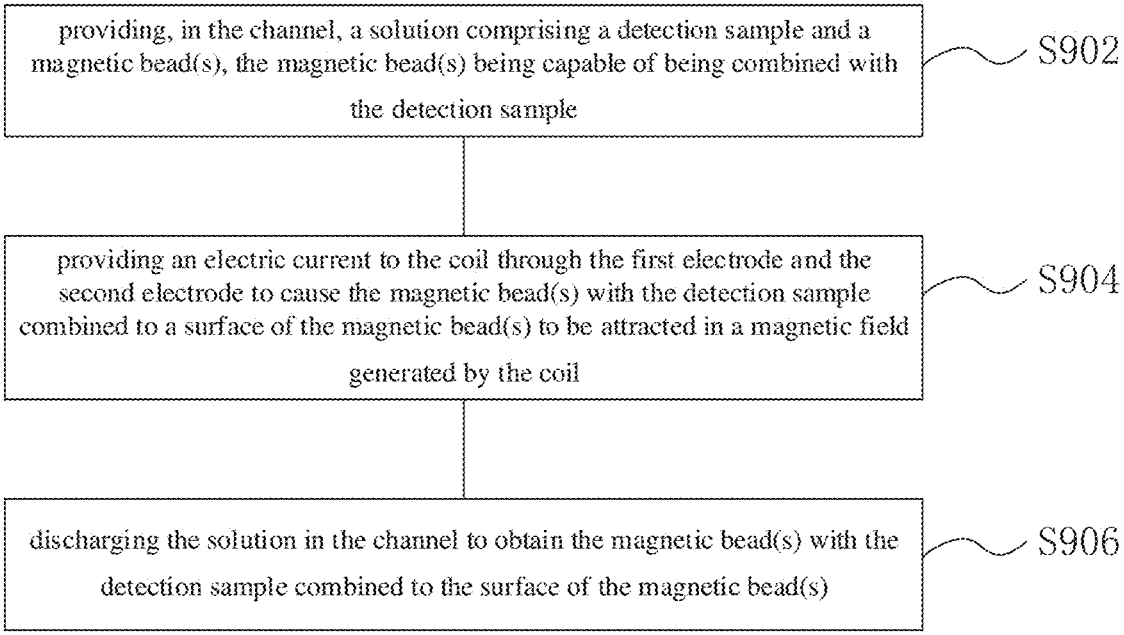
FIG. 9 is a schematic flow chart of a detection method for the microfluidic device according to some embodiments of the present disclosure.

FIG. 9 is a detection method 900 for any one of the above-mentioned microfluidic devices according to some embodiments of the present disclosure, which includes:

S902, providing, in the channel, a solution including a detection sample and a magnetic bead(s) which is capable of being bound with the detection sample;

S904, providing an electric current to the coil by the first electrode and the second electrode to attract the magnetic bead(s) with the detection sample bound to the surfaces of the magnetic bead(s) in a magnetic field formed by the coil; and S906, discharging the solution in the channel to obtain the magnetic bead(s) with the detection sample bound on the surfaces of the magnetic beads.

In the above-mentioned method, the magnetic bead is an example of the magnetic particle which may be a magnetic oxide particle, and the surface of the magnetic oxide particle may be coated with functional groups, thereby forming a special structured particle with certain magnetism.

The detection method according to some embodiments of the present disclosure will be described below in combination with chemiluminescence detection. In some embodiments, a solution including the detection sample and the magnetic beads is provided to the channel from the inlet of the channel of the microfluidic device, and the solution may be mixed by a mixing assist structure in the channel: an electric current is provided by the first electrode and the second electrode to the coils, and the magnetic beads with the target protein bound on the surfaces of the magnetic beads are attracted in a magnetic field formed by the energized coil; the solution in the channel of the microfluidic device is discharged; an enzyme-labeled secondary antibody reagent is provided to the channel from the inlet of the channel of the microfluidic device, and the providing of the current to the coil is stopped, so that the magnetic beads are released and may be mixed with the enzyme-labeled secondary antibody reagent; after the mixing operation, the current is supplied to the coil again by the first electrode and the second electrode, and the magnetic beads reacted with the enzyme-labeled secondary antibody reagent are attracted in the magnetic field formed by the energized coil; the solution in the channel of the microfluidic device is discharged; the chemiluminescence substrate is provided to the channel from the inlet of the channel of the microfluidic device, and the providing of the current to the coil is stopped, so that the magnetic beads are released and may be mixed with the chemiluminescence substrate; after the mixing operation, information such as the content of the detection sample may be obtained by detecting the fluorescence intensity in the channel of the microfluidic device.

It should be understood that the above description only takes chemiluminescence detection as an example to describe the detection method for a microfluidic device according to some embodiments of the present disclosure, however, the microfluidic device provided by the embodiments of the present disclosure can also be used to implement other immunoassays or molecular diagnoses, the embodiments of the present disclosure are not limited thereto.

The foregoing merely are exemplary embodiments of the disclosure, and not intended to define the scope of the disclosure, and the scope of the disclosure is determined by the appended claims.

What is claimed is:

1. A microfluidic device, comprising a first substrate and a second substrate, wherein the first substrate and the second substrate are oppositely arranged to define a channel between the first substrate and the second substrate, and the channel is configured for liquid to flow, the first substrate comprises a plurality of control assemblies which are arranged along an extending direction of the channel, each of the plurality of control assemblies comprises: a first electrode, a second electrode and a plurality of coils, and the first electrode is configured to input currents into the plurality of coils, and the plurality of coils are connected in parallel to the second electrode.

2. The microfluidic device according to claim 1, wherein the plurality of coils are arranged in a same layer in the first substrate, and the plurality of coils are arranged in a row in a direction perpendicular to the extending direction of the channel.

3. The microfluidic device according to claim 1, wherein the plurality of coils and the second electrode are arranged in different layers of the first substrate, and the second electrode is electrically connected to the plurality of coils through via holes.

4. The microfluidic device according to claim 1, wherein the first electrode and the plurality of coils are arranged in a same layer of the first substrate.

5. The microfluidic device according to claim 1, wherein the first electrode and the plurality of coils are arranged in different layers of the first substrate, and the first electrode is electrically connected to the plurality of coils through via holes.

6. The microfluidic device according to claim 1, wherein a resistivity of a material of at least one of the first electrode and the second electrode is smaller than a resistivity of a material of the plurality of coils.

7. The microfluidic device according to claim 1, wherein the plurality of control assemblies share a same electrode as the first electrode of each of the plurality of control assemblies.

8. The microfluidic device according to claim 1, wherein the plurality of control assemblies share a same planar electrode as the second electrode of each of the plurality of control assemblies.

9. The microfluidic device according to claim 8, wherein a plurality of the control assemblies used for a plurality of the channels share a same planar electrode as the second electrode of each of the plurality of the control assemblies.

10. The microfluidic device according to claim 8, wherein the planar electrode is a slit electrode.

11. The microfluidic device according to claim 8, wherein the planar electrode overlaps with the plurality of coils of each of the plurality of control assemblies in a direction perpendicular to a surface of the first substrate.

12. The microfluidic device according to claim 1, further comprising a mixing assist structure, wherein the mixing assist structure is in the channel and configured to mixing the fluid.

13. The microfluidic device according to claim 12, wherein the mixing assist structure is on one selected from a group consisting of:
    a surface of the second substrate facing the first substrate; and
    a surface of the substrate facing the second substrate.

14. The microfluidic device according to claim 12, wherein the mixing assist structure comprises a ∧-shaped protrusion, and the ∧-shaped rotrusion points to a direction opposite to a direction in which the fluid is allowed to flow.

15. The microfluidic device according to claim 12, wherein
    each of the channel comprises an inlet and an outlet,
    the mixing assist structure comprises a ∧-shaped protrusion, and
    the ∧-shaped protrusion points to the inlet of the channel in which the ∧-shaped protrusion is located.

16. The microfluidic device according to claim 12, wherein the mixing assist structure is arranged at at least one selected from a group consisting of:
    a position before at least one of the plurality of control assemblies in a direction in which the fluid is allowed to flow; and
    a position after at least one of the plurality of control assemblies in a direction in which the fluid is allowed to flow.

17. The microfluidic device according to claim 1, further comprising: a spacer,
    wherein the spacer is at opposite sides of the channel and between the first substrate and the second substrate, and
    the spacer, the first substrate and the second substrate define the channel.

18. A microfluidic detection assembly, comprising:
    the microfluidic device according to claim 1; and
    a magnetic particle, configured to move in the channel of the microfluidic device in an operation.

19. A detection method for a microfluidic device, the microfluidic device comprising a first substrate and a second substrate, wherein the first substrate and the second substrate are oppositely arranged to define a channel between the first substrate and the second substrate, and the channel is configured for liquid to flow,
    the first substrate comprises a plurality of control assemblies which are arranged along an extending direction of the channel, each of the plurality of control assemblies comprises: a first electrode, a second electrode and a plurality of coils, and
    the first electrode is configured to input currents into the plurality of coils, and the plurality of coils are connected in parallel to the second electrode,
    the detection method comprising:
        providing, in the channel, a solution comprising a detection sample and a magnetic particle, the magnetic particle being capable of being bound with the detection sample;
        providing an electric current to the coil through the first electrode and the second electrode to cause the magnetic particle with the detection sample bound to a surface of the magnetic particle to be attracted in a magnetic field generated by the coil; and
        discharging the solution in the channel to obtain the magnetic particle with the detection sample bound to the surface of the magnetic particle.

20. The microfluidic device according to claim 2, wherein the plurality of coils and the second electrode are arranged in different layers of the first substrate, and
    the second electrode is electrically connected to the plurality of coils through via holes.

* * * * *